United States Patent [19]

Nyman et al.

[11] Patent Number: 5,423,884
[45] Date of Patent: Jun. 13, 1995

[54] MEDICAL ELECTRODE AND ELECTRODE IMPLANTATION DEVICE

[75] Inventors: Per Nyman, Djursholm; Ulf Lindegren, Enskede, both of Sweden

[73] Assignee: Siemens Elema AB, Solna, Sweden

[21] Appl. No.: 108,514

[22] Filed: Aug. 18, 1993

[30] Foreign Application Priority Data

Aug. 28, 1992 [SE] Sweden .................. 9202480

[51] Int. Cl.⁶ .................. A61N 1/05
[52] U.S. Cl. .................. 607/127; 607/122
[58] Field of Search .................. 607/122, 125–127; 128/642

[56] References Cited

U.S. PATENT DOCUMENTS

| | | | |
|---|---|---|---|
| 3,428,046 | 2/1969 | Remer et al. | 607/122 X |
| 4,026,303 | 5/1977 | Babotai | 607/127 |
| 4,136,703 | 1/1979 | Wittkampf. | |
| 4,402,328 | 9/1983 | Doring. | |
| 4,407,303 | 10/1983 | Akerström. | |
| 4,550,737 | 11/1985 | Osypka. | |
| 4,677,990 | 7/1987 | Neubauer. | |

FOREIGN PATENT DOCUMENTS 3414072 10/1985 Germany .................. 607/126

*Primary Examiner*—Lee S. Cohen
*Attorney, Agent, or Firm*—Hill, Steadman & Simpson

[57] ABSTRACT

A medical electrode for intracorporeal electrical stimulation of body tissue, particularly for intracardial stimulation of heart tissue, includes an electrode cable having an elongated, flexible conductor covered with insulation, and terminating at one end with an electrode head for contact with body tissue. An opposite end of the cable is connectable to a source of therapeutic electrical energy. The exterior surface of the insulation is provided with a helical element winding around a substantial portion of the length of the cable between the opposite ends. The helical element may be a thin-like projection, or a groove. A device for rotating the cable during implantation causes the cable, by virtue of the helical element, to be advanced through a vein.

5 Claims, 2 Drawing Sheets

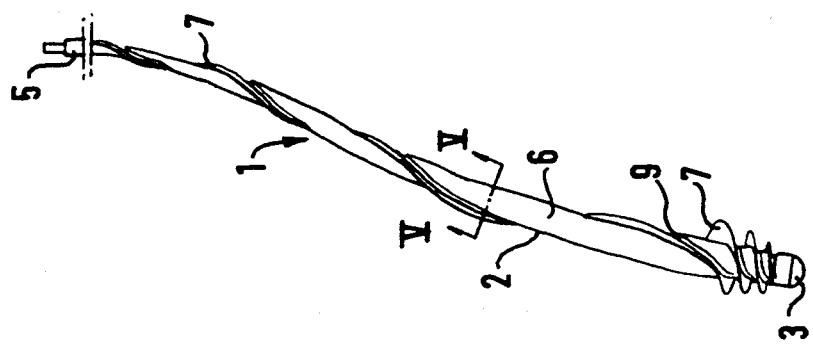
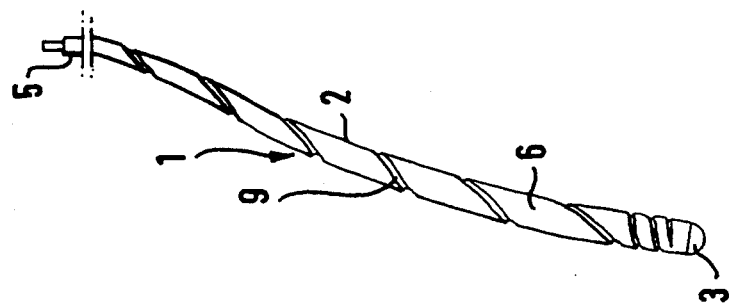
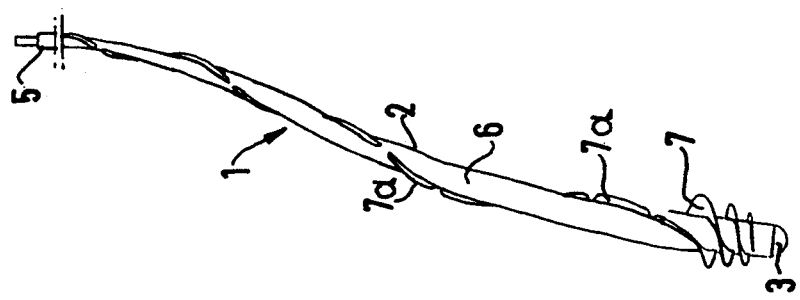
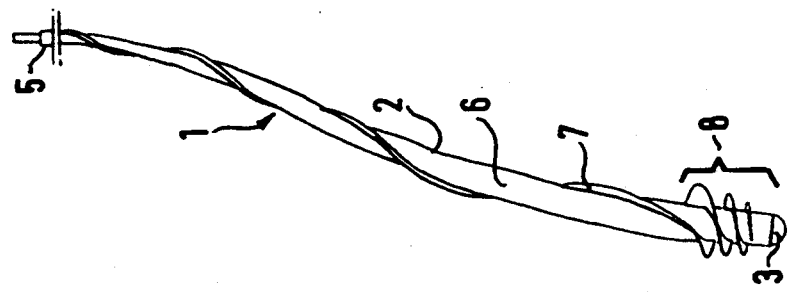

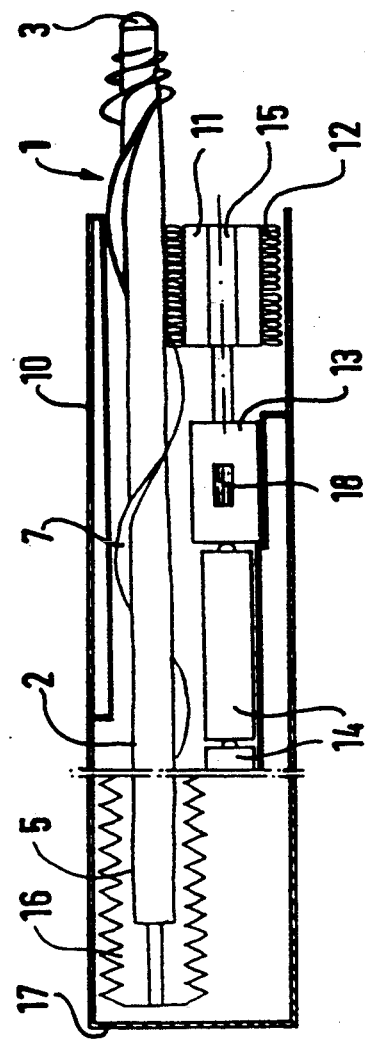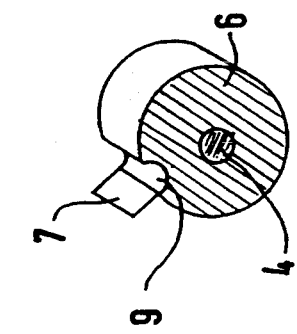

MEDICAL ELECTRODE AND ELECTRODE IMPLANTATION DEVICE

BACKGROUND OF THE INVENTION

1. Field of the Invention

The present invention relates to a medical electrode for intracorporeal stimulation of body tissue, particularly for intracardial stimulation of heart tissue, and to a device for implanting such an electrode.

2. Description of the Prior Art

Electrodes for medical purposes are generally known which include an electrode cable containing at least one elongated flexible conductor terminating in an electrode head at a distal end of the cable (as used herein, "distal" means distal from a yet-to-be-connected source of therapeutic electrical energy, and "proximate" means the end of the cable closer to that source). The electrode cable is provided with a layer of insulation.

It is of great importance for the electrode cable to be sufficiently pliant so that it is able, during advancement, for example, to heart of a patient via a vein, to follow the course of the vein without damaging the venous wall. The electrode cable is conventionally introduced using a stylet which is inserted into a channel in the cable. The stylet consists of a material having a sufficient stiffness required to advance the cable through the vein. At difficult passages, for example, where the cable must bend sharply, the stylet is often slightly retracted, so that the distal end of the electrode cable displays maximum pliancy. After such a passage has been negotiated, the stylet is again advanced to the distal end of the electrode cable in order to push the end into, for example, the atrium or into the ventricle, until the electrode head comes into contact with the heart wall for stimulation of the heart. Advancing the electrode cable in a vein with the aid of a stylet, which temporarily makes the electrode cable relatively stiff, is therefore not a simple procedure for the operator. Medical electrodes of the above-described type, wherein the cable is advanced through a vein with the aid of a stylet, are described in U.S. Pat. Nos. 4,136,703, 4,402,328 and 4,677,990.

SUMMARY OF THE INVENTION

It is an object of the present invention to provide a medical electrode of the type having an electrode cable containing a conductor covered with insulation, which has sufficient pliancy and elasticity to be advanced through a vein by relatively simple means, and without the need for a stylet.

The above object is achieved in accordance with the principles of the present invention in a medical electrode having a cable containing an electrical conductor covered by an insulation layer, wherein the external surface of the insulation layer carries helical means for imparting rotation to the cable around the longitudinal axis (i.e, the axis extending from the proximal end to the distal end of the cable) as the cable is being advanced through a vein. As the cable is rotated around its longitudinal axis, the cable screws itself forward through a vein with the aid of the helical means. The helical means wind around the exterior surface of the insulation for a substantial portion of the cable between the proximal and distal ends. Since the electrode cable does not require a channel for the stylet, the diameter of the cable can be made relatively small, and the electrode cable can retain its pliancy during implantation, since there is no need for the use of a stylet.

In a preferred embodiment of the invention, the helical means are formed by at least one fin-like element projecting from the surface of the insulation layer. The height of the fin-like element on the electrode cable can vary, so that the portion of the fin-like element at the distal end of the cable is, for example, higher than on the rest of the cable. The fin-like element can be divided into a plurality of short or long fins, disposed discontinuously on the surface of the insulation layer, but forming in combination a helical configuration. Such a structure is advantageous if some portion of the electrode cable must be more pliant than the rest of the cable. The fins can alternatively be devised so as to collapse against the insulation layer in a "standby" position, but will project from the surface when acted upon by blood in the vein.

In another embodiment of the invention, the helical means is formed by at least one groove in the layer of insulation. The electrode cable in this embodiment can thus be made extremely narrow. The profile of the groove determines how effectively the electrode cable can be screwed forward inside a vein.

In a further embodiment of the invention, the helical means is formed by at least one projecting, fin-like element and at least one groove in the insulation layer, running parallel to one other. In this embodiment, very effective cable advancement is obtained when the cable is rotated.

The pitch of the helical means in a further embodiment is less at the distal end of the electrode cable than along the remainder of the electrode cable. This embodiment results in effective screw advancement of the electrode cable, and also provides good anchoring of the electrode head to the heart wall when the helical means is screwed into the trabeculae.

The invention also includes a device for cooperating with the electrode cable for imparting rotation to the electrode cable. The device includes a motor-powered rotor having a rotary axis parallel to the longitudinal axis of the electrode cable. The rotor is equipped with members which engage the helical means on the electrode cable while the rotor is being rotated. These members transfer the rotary motion of the rotor to the cable by interaction with the helical means. Since the implantation device is not permanently fixed to the electrode cable, the operator can easily remove the device from the cable after the electrode cable has been implanted.

The member of the rotor which engages the helical means of the electrode cable can be formed by radially extending brushes (bristles) consisting of a material which is stiff enough to mechanically interact with the helical means to rotate the electrode cable, but which is incapable of damaging the cable.

DESCRIPTION OF THE DRAWINGS

FIGS., 1, 2, 3 and 4 respectively show perspective views of different embodiments of a medical electrode constructed in accordance with the principles of the present invention.

FIG. 5 is a cross-section through the medical electrode of FIG. 4, taken along line V—V.

FIG. 6 is a side view, partly in section, of a device for imparting rotation to any of the medical electrodes of FIGS. 1–4, constructed in accordance with the principles of the present invention.

DESCRIPTION OF THE PREFERRED EMBODIMENTS

A medical electrode 1 is shown in FIG. 1 of the type suited for intracardial stimulation of a heart. The medical electrode 1 includes an electrode cable 2 having a distal end terminating in an electrode head 3 for stimulating heart tissue in a patient. The electrode cable 2 contains a flexible conductor 4 (shown in FIG. 5) which runs from the proximal end 5 of the electrode cable 2 to the electrode head 3 at the distal end. The electrode cable 2 is provided with a layer of insulation 6 for the conductor 4. The external wall or surface of the layer of insulation 6 is provided with a projecting fin-like element 7, which is helically wound around a substantial portion of the entire length of the electrode cable 2 between the proximal end and the distal end. In the embodiment shown in FIG. 1, the pitch of the helical fin-like element 7 is less at the distal end 8 of the electrode cable 2 than along the rest of the electrode cable 2.

When the medical electrode 1 is implanted in a patient, rotation of the electrode cable 2 is imparted, for example, using a device of the type described below. This device also includes means which assist in advancing the electrode cable 2 in a vein. With the aid of the fin-like element 7, the electrode cable 2 can be screwed forward in this vein, until it reaches a desired end position. If the electrode head 3 is to be placed against the heart wall in the ventricle of a patient, the fin-like element 7 also serves as an anchoring element, permitting the distal end 8 of the electrode cable 2 to be screwed into trabeculae.

As shown in the embodiment of FIG. 2, the fin-like element 7 can be subdivided into a plurality of short or long fins 7a, which are discontinuously disposed on the surface of the insulation layer 6, but form in combination a helical configuration around the length of the electrode cable 2. Such a construction is advantageous if the electrode cable 2 must be more pliant than is the case in the embodiment of FIG. 1 with the fin-like element 7 being continuous.

In the embodiment of FIG. 3, the helical means is formed by a groove 9 in the surface of the insulation 6. The groove 9 helically winds around a substantial portion of the length of the electrode cable 2 between the proximal and distal ends. In the embodiment of FIG. 3, the pitch of the groove 9 is less than the pitch of the fin-like element 7 in FIG. 1 and the fins 7a in FIG. 2.

In the embodiment of FIG. 4, a fin-like element 7 is combined with a groove 9 in insulation layer 6, both running helically and parallel to each other around the electrode cable 2. FIG. 5 shows a cross-section through the electrode cable 2 in the embodiment of FIG. 4 in an enlargement. As a result of the construction of FIGS. 4 and 5, the electrode cable 2 can be advanced more rapidly in a vein during rotation. FIG. 5 also shows that the electrode cable can be made relatively thin, since no internal channel is needed for a stylet.

An example of a device for imparting rotation to the medical electrode 1 is shown in FIG. 6. The device can be a package 10, or a part of a package, for the medical electrode 1. The device includes a rotor 11 having radially extending brushes 12 disposed inside the packaging 10. The rotor 11 is rotated by a motor 13. The motor 13 can be provided with a speed control 18, and is preferably powered by batteries 14. The rotational axis 15 of the rotor 11 is parallel to the longitudinal axis of the packaged electrode cable 2. When the motor 12 causes the rotor 11 to rotate around the axis 15, the brushes 12 press on the insulation layer 6 and fin-like element 7 (or the groove 9) and thereby cause the electrode cable 2 to rotate around its longitudinal axis. The proximal end 5 of the electrode cable 2 in the packaging 10 is in the form of an extended bellows-shaped part 16, which can be detached from one of the walls 17 of the package 10 during implantation. The bellows-shaped part 16 can then be compressed to assist advancement of the rotating cable 2, so that it screws itself forward in a vein in the above-described manner.

The implantation device need not necessarily be a package, or a part of the package, for the medical electrode device 1, but may alternatively be a separate device in which the medical electrode device 1 is placed before implantation. The bellows-shaped part 16 may be replaced with any other type of component or combination of components for assisting advancement of the electrode cable 2.

The height, width, length and pitch of the fin-like element 7 on the electrode cable 2 in embodiments of FIGS. 1, 2 and 4 can be varied as needed, even on the same electrode cable 2. The groove 9 can similarly be made wider and deeper, as desired and needed, than is shown in the exemplary embodiments of FIGS. 3, 4 and 5.

Although other modifications and changes may be suggested by those skilled in the art, it is the intention of the inventors to embody within the patent warranted hereon all changes and modifications as reasonably and properly come within the scope of their contribution to the art.

We claim as our invention:

1. A medical electrode for intracorporeal stimulation of body tissue comprising:
    an electrode cable containing at least one elongated, flexible conductor and terminating at a first end of said electrode cable in an electrode head, said electrode cable having a second end and a layer of insulation covering said conductor and having an exterior surface; and
    helical means formed by at least one groove disposed in said exterior surface of said insulation layer and helically winding around a substantial portion of said electrode cable between said first and second ends for imparting rotation to said electrode cable around a longitudinal axis extending between said first and second ends.

2. A medical electrode for intracorporeal stimulation of body tissue comprising:
    an electrode cable containing at least one elongated, flexible conductor and terminating at a first end of said electrode cable in an electrode head, said electrode cable having a second end and a layer of insulation covering said conductor and having an exterior surface;
    helical means formed by at least one fin-like element projecting from said surface of said insulation layer and at least one groove in said insulation layer running parallel to said fin-like element, said fin-like element and said at least one groove helically winding around a substantial portion of said electrode cable between said first and second ends for imparting rotation to said electrode cable around a longitudinal axis extending between said first and second ends.

3. A medical electrode for intracorporeal stimulation of body tissue comprising:
- an electrode cable containing at least one elongated, flexible conductor and terminating at a first end of said electrode cable in an electrode head, said electrode cable having a second end and a layer of insulation covering said conductor and having an exterior surface;
- helical means disposed on said exterior surface of said insulation layer and helically winding around a substantial portion of said electrode cable between said first and second ends for imparting rotation to said electrode cable around a longitudinal axis extending between said first and second ends, said helical means having a pitch at said first end of said electrode cable which is less than a pitch of said helical means along a remainder of said electrode cable.

4. A medical electrode implantation system comprising:
- a medical electrode for intracorporeal stimulation of body tissue having an electrode cable containing at least one elongated, flexible conductor and terminating at a first end of said electrode cable in an electrode head, said electrode cable having a second end with a longitudinal axis extending between said first and second ends, and a layer of insulation covering said conductor and having an exterior surface;
- a helix disposed on said exterior surface of said insulation layer and helically winding around a substantial portion of said electrode cable between said first and second ends; and
- means for interacting with said helix for rotating said electrode cable, comprising a motor-powered rotor having a rotational axis parallel to said longitudinal axis of said cable, said rotor carrying members engaging said helix on said electrode cable when said rotor rotates.

5. A medical electrode implantation system as claimed in claim 4 wherein said members on said rotor comprise radially extending brushes.

* * * * *